United States Patent
Scholl et al.

[11] 3,934,019
[45] Jan. 20, 1976

[54] PESTICIDAL 4,5-BIS-(TRIFLUOROMETHYLIMINO)-DIAZOLES

[75] Inventors: Hans-Joachim Scholl, Cologne; Erich Klauke, Odenthal; Ferdinand Grewe, Burscheid; Ingeborg Hammann, Cologne, all of Germany

[73] Assignee: Bayer Aktiengesellschaft, Leverkusen, Germany

[22] Filed: Oct. 3, 1973

[21] Appl. No.: 403,296

Related U.S. Application Data

[63] Continuation-in-part of Ser. No. 206,159, Dec. 8, 1971, Pat. No. 3,787,435.

[30] Foreign Application Priority Data

Dec. 18, 1970 Germany............................ 2062346

[52] U.S. Cl. ................ 424/273; 424/251; 424/272
[51] Int. Cl.² ............................................ A01N 9/22
[58] Field of Search............................ 424/273, 251

[56] References Cited
UNITED STATES PATENTS

| | | | |
|---|---|---|---|
| 3,721,679 | 3/1973 | Singer | 424/273 |
| 3,773,960 | 11/1973 | Rutz et al. | 424/273 |
| 3,787,435 | 1/1974 | Scholl et al. | 424/273 |

OTHER PUBLICATIONS
Chemical Abstracts, Vol. 70, p. 4112f (1969).

*Primary Examiner*—V. D. Turner
*Attorney, Agent, or Firm*—Burgess, Dinklage & Sprung

[57] ABSTRACT

4,5-bis-(trifluoromethylimino)oxazoles or diazoles are prepared by reacting the enol form of an amide or an imide of a carboxylic acid or carbonic acid, having at least one hydrogen atom on each of an oxygen and nitrogen or two nitrogen atoms vicinal to the amide carbon atom, with perfluoro-2,5-diazahexa-2,4-diene in the presence of a hydrogen fluoride acceptor at a temperature of about −50° to 120°C, in accordance with the following formula

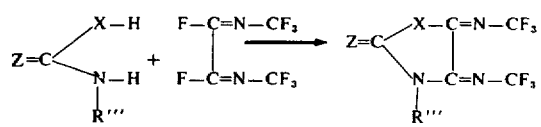

in which
Z is oxygen, R-N= or

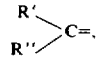

and
X is oxygen or

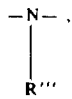

and
R, R', R'' and R''' each is hydrogen or various optionally substituted hydrocarbon or heterocyclic radicals, several of them together possibly forming a heterocyclic ring.

The invention also extends to compositions containing, and methods of using, the new compounds to combat fungi, insects and acarids.

18 Claims, No Drawings

PESTICIDAL 4,5-BIS-(TRIFLUOROMETHYLIMINO)-DIAZOLES

This application is a continuation-in-part of U.S. Pat. application Ser. No. 206,159, filed Dec. 8, 1971, now U.S. Pat. No. 3,787,435, issued Jan. 22, 1974.

The present invention relates to and has for its objects the provision of a process involving reacting the enol form of an amide of an imide of a carboxylic acid or carbonic acid, having at least one hydrogen atom on each of an oxygen and nitrogen or two nitrogen atoms vicinal to the amide carbon atom, with perfluoro-2,5-diazahexa-2,4-diene in the presence of a hydrogen fluoride acceptor at a temperature of about −50° to 120°C, to form 4,5-bis-(trifluoro-methylimino)-oxazoles or diazoles which are fungicidally, insecticidally and acaricidally active, with other and further objects of the invention becoming apparent from a study of the within specification and accompanying examples.

The present invention relates to the preparation of new 4,5-bis-trifluoromethyl-imino derivatives of sulfur-free heterocyclic five-membered rings with two ring hetero atoms of the general formula

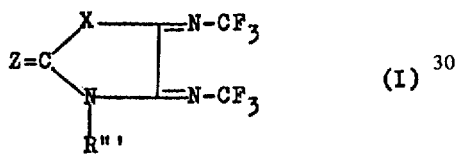
(I)

in which
Z is oxygen, R-N= or

X is oxygen or

and
R, R', R'' and R''' are each hydrogen; alkyl, alkenyl or alkynyl with up to 8 carbon atoms optionally substituted by halogen, cyano, lower alkoxy or alkylmercapto; optionally lower-alkyl substituted cycloalkyl; carbalkoxy; aralkyl with up to 2 carbon atoms in the alkyl moiety or aryl with up to 14 carbon atoms in the ring system, the aryl radicals optionally being substituted by halogen, cyano, nitro, lower alkyl, lower haloalkyl, lower alkoxy or lower alkylmercapto; 5- to 7-membered heterocyclic rings; or a radical which together with Z and X or the N-atom of the ring forms further 5- to 7-membered ring, the heterocyclic rings optionally being substituted with halogen, cyano, nitro or lower alkyl, or being fused with a benzene ring which is optionally partially hydrogenated.

In preparing the novel compounds, the enol form of an amide or an imide of a carboxylic acid or carbonic acid having at least one hydrogen atom on each of an oxygen and nitrogen or two nitrogen atoms vicinal to the amide carbon atom is reacted with perfluoro-2,5-diazahexa-2,4-diene in the presence of a hydrogen fluoride acceptor at a temperature of about −50° to 120°C. Specifically, a carbonic acid derivative or carboxylic acid derivative of the general formula

(II)

in which
X and Z have the meanings stated above, is reacted with perfluoro-2,5-diazahexa-2,4-diene of the formula

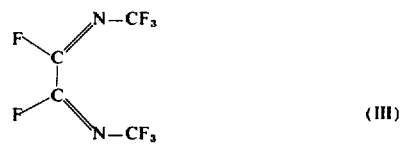
(III)

in the presence of a hydrogen fluoride acceptor at a temperature of about −50° to 120°C.

It is pointed out that the designation "sulfur-free" has reference to the heterocyclic five-membered ring shown in formula (I) rather than to the substituents which, as mentioned, may contain sulfur, e.g. alkylmercapto.

It is very surprising that the above-mentioned compounds of the formula (II) can react with perfluoro-2,5-diazahexa-2, 4-diene of the formula (III) to give the hitherto unknown five-membered ring systems of the formula (I) smoothly and with good yields. Furthermore it is suprising that the compounds according to the invention possess a fungicidal, insecticidal and acaricidal effectiveness. The provision of this new class of substances with valuable properties is of great technical importance.

If N,N'-dimethyl urea and perfluoro-2,5-diazahexa-2,4-diene are used as starting materials, and sodium fluoride is used as acid-binding agent, the reaction course can be represented by the following formula scheme:

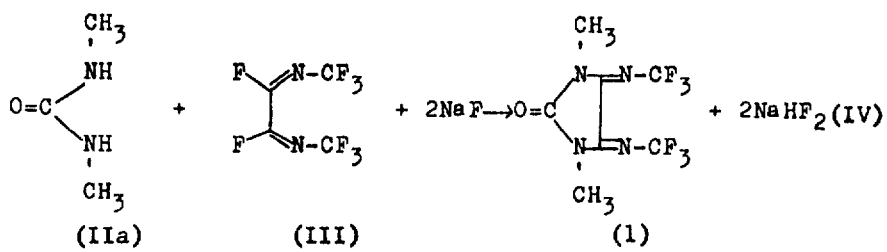

If 3-methyl-pyrazolone-(5), which reacts from its enol form, and perfluoro-2,5-diazahexa-2,4-diene are used as starting materials, and sodium fluoride is used as acid-binding agent, the reaction course can be represented by the following formula scheme:

As examples of primary amines, there are suitable, besides the amines on which the above isocyanates are based, the following amines for the preparation of compounds of the formula (II): 2-aminopyridine, 2-aminothiazole, 2-amino-benzthiazole, 2-amino-1-methyl-

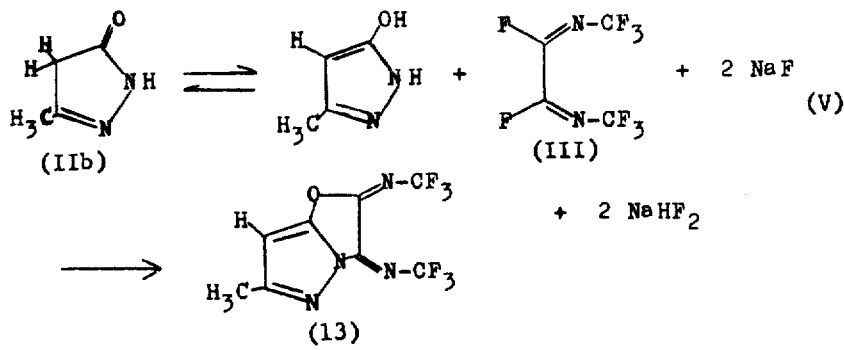

The carbonic acid derivative or carboxylic acid derivatives to be used as starting materials are defined generally by the formula (II).

Preferably R, R', R'', R''', and R'''' are hydrogen; alkyl or alkenyl with up to 6 carbon atoms, optionally substituted by fluorine, chlorine, bromine and/or alkylmercapto; cyclopentyl or cyclohexyl; carbomethoxy or other carbalkoxy groups containing from 2 to 5 carbon atoms in the alkoxy group; benzyl or aryl with up to 10 carbon atoms in the ring system, the aromatic rings possibly being substituted by fluorine, chlorine, bromine, cyano, nitro, methyl, ethyl, isopropyl, chloromethyl, trifluoromethyl, methoxy and/or methylmercapto; 5- or 6-membered heterocyclic rings or radicals which together with Z and X or the N-atom of the ring form a 5- or 6-membered ring, the heterocyclic rings optionally fused with a benzene ring which may be partially hydrogenated. Most preferably Z is oxygen and X is =N-R''', one R''' being methyl and the other being phenyl or cyclohexyl optionally substituted with chloro or trifluoromethyl.

The carbonic acid derivatives and carboxylic acid derivatives of the general formula (II) to be used as starting materials are for the most part known and can be prepared in generally known manner; they are obtained for example when carbonic acid halides or carboxylic acid halides are reacted with ammonia or amines; thus, many of the urea derivatives of the general formula (II) can be prepared in known manner from primary amines and isocyanates; there are mentioned for example the following isocyanates: p-trifluoromethyl-phenyl-isocyanate, p-nitrophenylyisocyanate, methylisocyanate, isopropylisocyanate, tert.-butylisocyanate, cyclohexylisocyanate, allylisocyanate, β-chloroethylisocyanate, phenylisocyanate, o-nitrophenylisocyanate, p-nitrophenylisocyanate, m-nitrophenylisocyanate, o-chloro-phenylisocyanate, m-chlorophenylisocyanate, 3,4-dichloro-phenylisocyanate, p-chlorophenylisocyanate, β-naphthylisocyanate, benzylisocyanate, stearylisocyanate, β-cyano-ethylisocyanate, ethylisocyanate, n-propylisocyanate, n-butylisocyanate, isobutylisocyanate, 2-ethyl-hexylisocyanate, dodecylisocyanate, tetradecylisocyanate, hexadecylisocyanate, p-methoxy-phenylisocyanate, p-methylmercapto-phenylisocyanate; and the like.

cyclohexane, hexahydro-benzylamine, 2-chloro-aniline, 3-nitroaniline, 2-chloro-4-nitroaniline, 5-chloro-2-amino-toluene, 4-chloro-3-amino-benzotrifluoride, 1-amino-2-phenyl-ethane, 2-amino-1-isopropylbenzene, 5-amino-1,2,4-trimethylbenzene, 5,6,7,8-tetrahydronaphthylamine-(1), 3,5-dichloroaniline, 2,4,5-trichloroaniline, 2,4-dichloroaniline, 2,3-dichloroaniline, 2,5-dichloroaniline, 3-chloroaniline, 4-chloroaniline, 4-chloro-2-nitroaniline, aniline, 2-nitroaniline, 4-nitroaniline, 5-chloro-2-nitroaniline, 4-chloro-3-nitroaniline, 3-chloro-4-nitroaniline, 4,6-dichloro-2-nitroaniline, 2,5-dichloro-4-nitroaniline, 2,6-dichloro-4-nitroaniline, 2-amino-toluene, 3-chloro-2-aminotoluene, 4-chloro-2-amino-toluene, 5-nitro-4-amino-1,3-dimethyl-benzene, 6-nitro-4-amino-1,3-dimethyl-benzene, 5-amino-1,3-dimethyl-benzene, 5-amino-1,3-bis-trifluoromethyl-benzene, 2-amino-1,4-dimethyl-benzene, 2-amino-1-methyl-3-ethylbenzene, 6-amino-1,2,4-trimethyl-benzene, 2-amino-1,3,5-trimethyl-benzene, 2-amino-1,3-diethyl-benzene, 4-amino-1,3-dimethyl-5-ethyl-benzene, 4-amino-1-methyl-3,5-diethyl-benzene, 2-amino-1,3-diisopropylbenzene, 5,6,7,8-tetrahydronaphthylamine-(2), β-bromo-ethylamine, 1-cyano-1-phenyl-ethylamine, 1-cyano-1-methyl-ethylamine, 5-chloro-2-amino-benzo-trifluoride, 6-chloro-2-amino-toluene, 4,5-dichloro-2-amino-toluene, 3-nitro-2-amino-toluene, 4-nitro-2-amino-toluene, 5-nitro-2-amino-toluene, 6-nitro-2-amino-toluene, 4-chloro-5-nitro-2-amino-toluene, 3-amino-toluene, 4-chloro-3-amino-toluene, 6-chloro-3-amino-toluene, 4,6-dichloro-3-amino-toluene 4-amino-toluene, 2-chloro-4-amino-toluene, 2-nitro-4-amino-toluene, 3-nitro-4-amino-toluene, 2-amino-1-ethylbenzene, 1-amino-1-phenyl-ethane, 2,3-dimethylaniline, 2,6-dimethyl-aniline, 3,4-dimethylaniline, 2,4-dimethylaniline, and the like.

The guanidines of the formula (II), such as 2-aminobenzimidazole, 2-[amino-(carbomethoxy)]-benzimidazole, p-chlorophenylimido-N,N'-diethyl urea, are obtainable in manner known from the literature.

The perfluoro-2,5-diazahexa-2,4-diene of the formula (III) to be used as starting material is known (J. Am. Chem. Soc. 89, 5007 (1967)).

The reaction may be carried out in the presence of a diluent. As diluents, all inert organic solvents are suitable. Preferred solvents include hydrocarbons, such as benzine, benzene and toluene; nitriles, such as acetonitrile; and chlorinated hydrocarbons, such as methylene chloride, chloroform and chlorobenzene.

As acid-binders, all customary acid-binding agents can be used. There may be mentioned: alkali metal carbonates, alkali metal bicarbonates and tertiary amines, such as triethylamine, dimethylaniline, and the like. In particular the alkali metal fluorides, especially sodium fluoride, have proved to be hydrogen fluoride acceptors which are particularly useful in practice.

The reaction temperatures can be varied within a fairly wide range. In general, the reaction is carried out at about −50° to 120°C, preferably about −30° to 90°C.

In carrying out of the process according to the invention, for each mole of the compound of formula (II) there is generally used 1 mole of perfluoro-2,5-diazahexa-2,4-diene of the formula (III); the alkali metal fluoride is desirably used in excess, e.g. about 3 to 4 moles, but amounts lesser or greater than the stated proportions by up to 20 per cent by weight can be used without substantial lowering of the yield. Expediently, the perfluoro-2,5-diazahexa-2,4-diene is added dropwise to a suspension comprising the compound of formula (II), organic solvent and hydrogen fluoride acceptor. Filtration from the fluoride is then effected, followed by concentration and recrystallization. Another method of working up consists in adding water to the reaction mixture and, optionally, recrystallizing the residue obtained.

The active compounds of the invention exhibit a strong fungitoxic activity. In the concentrations appropriate for the control of fungi, they generally do not damage cultivated plants and they have a low toxicity to warm-blooded animals. For these reasons, they are suitable for use as crop protection agents for the control of fungi. Fungitoxic agents in crop protection are used for the control of archimycetes, Phycomycetes, Ascomycetes, Basidiomycetes and Fungi Imperfecti.

The active compounds of the invention have a broad activity spectrum and can be applied against parasitical fungi which infect above-the-ground parts of plants or attack the plants from the soil, as well as against seed-borne pathogenic agents.

The compounds possess a good activity against *Fusicladium dendriticum*, the causative organism of apple scab, against *Phytophthora infestans*, the causative organism of potato blight, and against *Piricularia oryzae*, the causative organism of rice blast.

The compounds according to the invention, however, also act against other fungi which attack rice or other cultivated plants, such as *Mycosphaerella musicola*, *Verticillium alboatrum*, *Phialophora cinerescens* and *Fusarium species*.

The compounds according to the invention are distinguished by an extraordinarily high degree of activity and a very broad spectrum against phytopathogenic soil fungi and against seed-borne fungal plant diseases. They can be used preferably as soil treatment agents and seed dressings and are superior in this respect to customary commercial preparations. Surprisingly, the present active compounds show not only a protective activity, but also a curative and systemic effect.

The compounds which can be prepared according to the process also possess an insecticidal and acaricidal effectiveness. The products are used with success in crop protection for the control of noxious sucking and biting insects, Diptera and mites (Acarina), as well as in the veterinary and hygiene field; further, in the protection of stored products against a multiplicity of animal pests such as endoparasites and ectoparasites.

To the sucking insects contemplated herein there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*; and the like.

In the case of the biting insects contemplated herein, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar *Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia Kühniella*) and greater wax moth (*Galleria mellonella*); and the like.

With the mites (Acari) there are classed, in particular, the spider mites (Tetranychidae) such as the two-spotted spider mite (*Tetranychus telarius = Tetranychus althaeae* or *Tetranychus urticae*) and the European red mite (Paratetranychus pilosus = Panonychus ulmi), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*); and the like.

The active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide formulations or compositions, e.g. conventional pesticide dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes), cycloalkanes (e.g. cyclohexane, etc), paraffins (e.g. petroleum or mineral oil fractions), chlorinated aliphatic hydrocarbons (e.g. methylene chloride, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), ketones (e.g. acetone, methyl ethyl ketone, methyl isobutyl ketone, cyclohexanone, etc.), and/or water: as well as inert dispersible finely divided solid carriers, such as ground natural minerals (e.g. kaolins, alumina, silica, chalk, i.e., calcium carbonate, talc, kieselguhr, etc.) and ground synthetic minerals (e.g. highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides or acaricides, insecticides, herbicides, bactericides, nematicides, fertilizers, growth regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95%, and preferably 0.5–90%, by weight of the mixture, whereas carrier composition mixtures suitable for direct application or field application generally contemplate those in which the active compound is present in an amount substantially between about 0.0001–10%, preferably at least 0.5% weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.1–95%, and preferably 0.5–95% by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of active compound or even the 100% active substance alone, e.g. about 20–100% by weight of the active compound.

In the case of seed treatment, in general amounts of active compound of 0.01 to 50 g, preferably 0.01 to 5 g, per kilogram of seed are applied as a seed dressing.

For soil treatment, in general amounts of active compound of 1 to 500 g, preferably 10 to 200 g, are applied per cubic meter of soil. The concentrations of active compound in the ready-to-apply preparations may vary very greatly. In general, they are from 0.0001 to 95%.

Furthermore, the present invention contemplates methods of selectively killing, combating or controlling pests, e.g. fungi, insects and acarids, which comprise applying to at least one of correspondingly (a) such fungi, (b) such insects, (c) such acarids and (d) the corresponding habitat thereof, i.e., the locus to be protected, a correspondingly combative or toxic amount, i.e. a fungicidally, insecticidally, or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, sprinkling, pouring, via dressings, incrustations, and the like.

It will be realized, of course, that the concentration of the particular active compound utilized in admixture with the carrier vehicle will depend upon the intended application. Therefore, in special cases, it is possible to go above or below the aforementioned concentration ranges.

The unexpected superiority and outstanding fungicidal and acaricidal activity of such active compounds usable according to the present invention is illustrated, without limitation, by the following Examples.

EXAMPLE 1

Mycelium growth test

| 20 parts by weight agar-agar | 5 parts by weight acetone |
| 200 parts by weight potato decoction | 2 parts by weight $Na_2HPO_4$ |
| 5 parts by weight malt | 0.3 parts by weight $Ca(NO_3)_2$ |
| 15 parts by weight dextrose | |

Proportion of solvent to nutrient medium:
2 parts by weight acetone
100 parts by weight agar nutrient medium The amount of active compound required for the desired concentration of active compound in the nutrient medium is mixed with the stated amount of solvent.

The concentrate is thoroughly mixed in the stated proportion with the liquid nutrient medium which has been cooled to 42°C and is then poured into Petri dishes of 9 cm diameter. Control dishes to which the preparation has not been added are also set up.

When the nutrient medium has cooled and solidified, the dishes are inoculated with the species of fungi stated in the Table and incubated at about 21°C.

Evaluation is carried out after 4–10 days, dependent upon the speed of growth of the fungi. When evaluation is carried out the radial growth of the mycelium on the treated nutrient media is compared with the growth on the control nutrient media. In the evaluation of the fungus growth, the following characteristic values are used:

| | |
|---|---|
| 0 | no fungus growth |
| 1 | very strong inhibition of growth |
| 2 | medium inhibition of growth |
| 3 | slight inhibition of growth |
| 4 | growth equal to that of untreated control. |

The active compounds, their concentrations and the results obtained can be seen from Table 1.

EXAMPLE 2

Fusicladium test (apple scab) (Protective)

| | |
|---|---|
| Solvent: | 4.7 parts by weight acetone |
| Emulsifier: | 0.3 parts by weight alkylaryl polyglycol ether |
| Water: | 95 parts by weight |

The amount of active compound required for the desired concentration of the active compound in the spray liquid is mixed with the stated amount of solvent, and the concentrate is diluted with the stated amount of water which contains the stated additions.

Young apple seedlings in the 4–6 leaf stage are sprayed with the spray liquid until dripping wet. The plants remain in a greenhouse for 24 hours at 20°C and at a relative atmospheric humidity of 70%. They are then inoculated with an aqueous conidium suspension of the apple scab causative organism (*Fusicladium dendriticum Fuckel*) and incubated for 18 hours in a humidity chamber at 18°–20°C and at a relative atmospheric humidity of 100%.

Table 1

| | | Mycelium growth test | | | | | | | | | | | |
|---|---|---|---|---|---|---|---|---|---|---|---|---|---|
| Active compounds | | Concentration of active compound ppm | A | B | C | D | E | F | G | H | I | J | K |
| 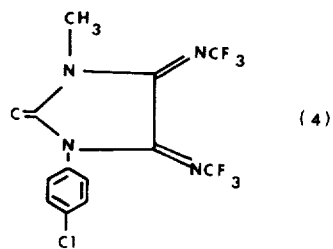 | (4) | 10 | – | – | – | – | – | 0 | 0 | 0 | – | 0 | 0 |
| 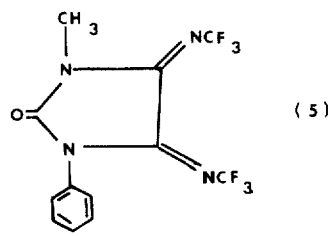 | (5) | 10 | – | – | – | – | – | – | 0 | – | – | – | 0 |

A *Botrytis cinerea*
B *Cochliobolus miyabeanus*
C *Fusarium oxysp. f. cubense*
D *Fusarium oxysp. f. dianthi*
E *Pellicularia sasakii*
F *Verticillium albo-atrum*
G *Colletotrichum ceffeanum*
H *Phialophora cinerescens*
I *Cercospora personata*
J *Mycosphaerella musicola*
K *Piricularia oryzae*

The plants are then again placed in a greenhouse for 14 days.

15 days after inoculation, the infection of the seedlings is determined as a percentage of the untreated but also inoculated control plants.

0% means no infection; 100% means that the infection is exactly as great as in the case of the control plants.

The active compounds, the concentrations of the active compounds and the results can be seen from Table 2(a) & (b).

Table 2(a)

Fusicladium test / Protective

| Active Compound | Infection as a percentage of the infection of the untreated control with a concentration of active compound (in %) of | |
|---|---|---|
| | 0.0062 | 0.00156 |
| 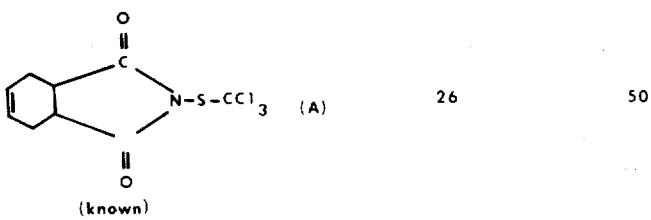 (A) (known) | 26 | 50 |
| 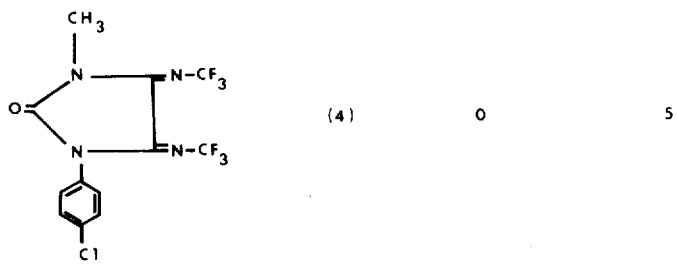 (4) | 0 | 5 |
| 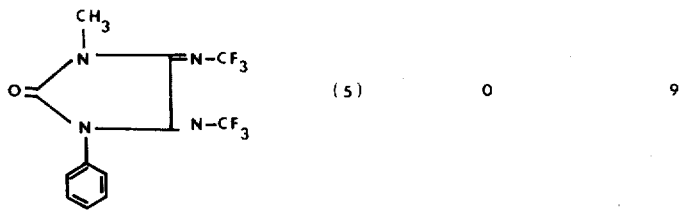 (5) | 0 | 9 |
| 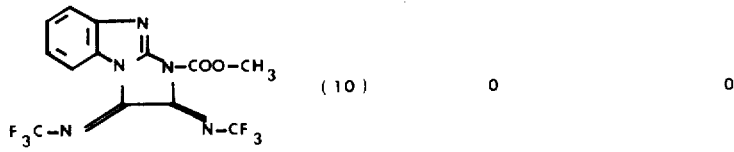 (10) | 0 | 0 |
| 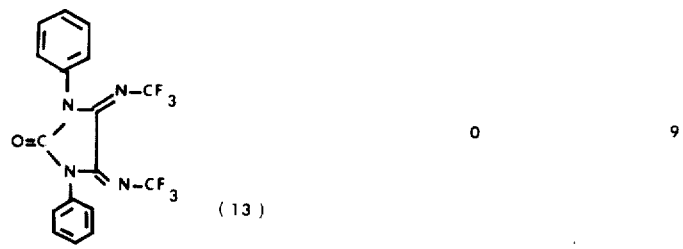 (13) | 0 | 9 |
|  (8) | 0 | 6 |

Table 2 (b)

Fusicladium test Protective

| Active Compound | Infestation as a percentage of the infection of the untreated control with a concentration of active compound (in %) of 0.0025 |
|---|---|
| 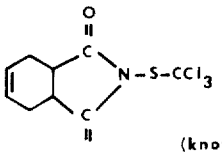 (known) | 34 |
| 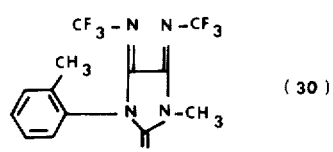 (30) | 0 |
| 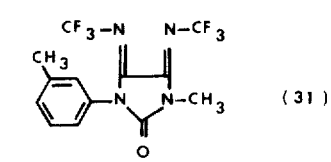 (31) | 0 |
| 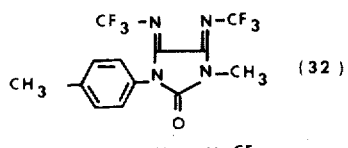 (32) | 1 |
| 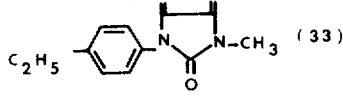 (33) | 2 |
| 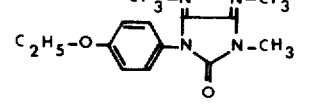 (35) | 0 |
| 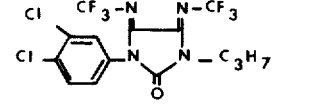 (47) | 0 |
| 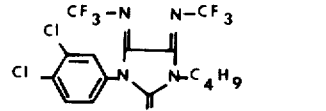 (49) | 0 |

EXAMPLE 3

Fusicladium test (apple scab) [Curative]

Solvent: 4.7 parts by weight acetone
Emulsifier: 0.3 parts by weight alkylaryl polyglycol ether
Water: 95 parts by weight.

The amount of active compound required for the desired concentration of the active compound in the spray liquid is mixed with the stated amount of solvent, and the concentrate is diluted with the stated amount of water which contains the stated additions.

Young apple seedlings in the 4–6 leaf stage are inoculated with an aqueous conidium suspension of the apple scab causative organism *Fusicladium dendriticum* Fuckel and incubated for 18 hours in a humidity chamber at 18°–20°C and at an atmospheric humidity of 100%. The plants are then placed in a greenhouse where they dry.

After standing for a suitable period of time, the plants are sprayed dripping wet with the spray liquid prepared in the manner described above. The plants are then returned to a greenhouse.

15 days after inoculation, the infestation of the apple seedlings is determined as a percentage of the untreated but also inoculated control plate.

0% means no infestation; 100% means that the infestation is exactly as great as in the case of the control plants.

The active compounds, the concentrations of the active compounds, the period of time between inoculation and spraying and the results obtained can be seen from Table 2.

relative atmospheric humidity of 100%. The plants are then returned to a greenhouse for 14 days.

15 days after inoculation, the infection of the seedlings is determined as a percentage of the untreated but also inoculated control plants. 0% means no infection; 100% means that the infection is exactly as great as in the case of the control plants.

The active compounds, the concentrations of the active compounds and the results obtained can be seen from Table 4.

Table 3
Fusicladium Test/curative

| Active compound | Residence period in hours | Infestation as a percentage of the infection of the untreated control with a concentration of active compound (in %) of | |
|---|---|---|---|
| | 42 | 0.025 | 0.0062 |
| $C_{12}H_{25}NH-C(=NH)(NH_2) \cdot CH_3COOH$ (known) | | 57 | — |
| [structure with benzimidazoline, $F_3C-N$, $N-CF_3$, $N-COO-CH_3$] (10) | | 0 | 14 |

Table 4
Fusicladium-Test/systemic

| Active Compound | Infestation as a percentage of the infection of the untreated control with a concentration of active compound of |
|---|---|
| | 15 ppm |
| [structure with benzimidazoline, $F_3C-N$, $N-CF_3$, $N-COO-CH_3$] (10) | 5 |

EXAMPLE 4

Fusicladium test (systemic)

| Solvent: | 4.7 parts by weight acetone |
| Emulsifier: | 0.3 parts by weight alkylarylpolyglycol ether |
| Water: | 95 parts by weight |

The amount of active compound required for the desired concentration of the active compound in the liquid to be used for watering is mixed with the stated amount of solvent, and the concentrate is diluted with the stated amount of water which contains the stated additions.

Apple seedlings grown in standard soil are, in the 3–4 leaf stage, watered once in one week with 20 cc of the liquid to be used for watering, in the stated concentration of active compound, with reference to 100 cc of soil. The plants so treated are, after the treatment, inoculated with an aqueous conidium suspension of *Fusicladium dendriticum* Fuckel and incubated for 18 hours in a humidity chamber at 18°–20°C and at a

EXAMPLE 5

Phytophthora test

| Solvent: | 4.7 parts by weight of acetone |
| Dispersing agent: | 0.3 parts by weight of alkylarylpolyglycol ether |
| Water: | 95 parts by weight |

The amount of the active compound required for the desired concentration of the active compound in the spray liquid is mixed with the stated amount of solvent and the concentrate is diluted with the stated amount of water which contains the stated additions.

Young tomato plants (Bonny best) with 2–6 foliage leaves are sprayed with the spray liquid until dripping wet. The plants remain in a greenhouse for 24 hours at 20°C and at a relative atmospheric humidity of 70%. The tomato plants are then inoculated with an aqueous spore suspension of *Phytophthora infestans*. The plants are brought into a moist chamber with an atmospheric humidity of 100% and a temperature of 18–20°C.

After 5 days the infestation of the tomato plants is determined as a percentage of the untreated but likewise inoculated control plants: 0% means no infestation; 100% means that the infestation is exactly as great as in the case of the control plants.

The active compounds, the concentrations of the active compounds and the results can be seen from the following Table:

Table 5

Phytophthora test

| Active compound | | Infection as a percentage of the infection of the untreated control with a concentration of active compound (in %) of | |
|---|---|---|---|
| | | 0.0062 | 0.0031 |
| [structure: CH₂-NH-C(=S)-S / Zn \ S-C(=S)-NH-CH₂] (known) | (B) | 23 | 41 |
| [structure with CH₃, N-CF₃ groups, Cl-phenyl] | (4) | 2 | 6 |
| [structure: CF₃-N, N-CF₃, phenyl, -(CH₂)₅-CN] | (25) | 7 | — |
| [structure with CH₃, N-CF₃ groups, dichlorophenyl] | (8) | 5 | 23 |

EXAMPLE 6

Podosphaera test (powdery mildew of apples) [Protective]

Solvent: 4.7 parts by weight acetone
Emulsifier: 0.3 parts by weight alkylaryl polyglycol ether
Water: 95 parts by weight The amount of active compound required for the desired concentration of the active compound in the spray liquid is mixed with the stated amount of solvent, and the concentrate is diluted with the stated amount of water which contains the stated additions.

Young apple seedlings in the 4–6 leaf stage are sprayed with the spray liquid until dripping wet. The plants remain in a greenhouse for 24 hours at 20°C and at a relative atmospheric humidity of 70%. They are then inoculated by dusting with conidia of the apple powdery mildew causative organism (*Podosphaera leucotricha* Salm.) and placed in a greenhouse at a temperature of 21°–23°C and at a relative atmospheric humidity of about 70%.

Ten days after the inoculation, the infestation of the seedlings is determined as a percentage of the untreated but also inoculated control plants.

0% means no infestation; 100% means that the infestation is exactly as great as in the case of the control plants.

The active compounds, the concentrations of the active compounds and the results obtained can be seen from the following Table 4:

Table 6

Podosphaera test/Protection

| Active compound | Infection as a percentage of the infection of the untreated control with a concentration of active compound (in %) of | |
|---|---|---|
| | 0.0062 | 0.00156 |

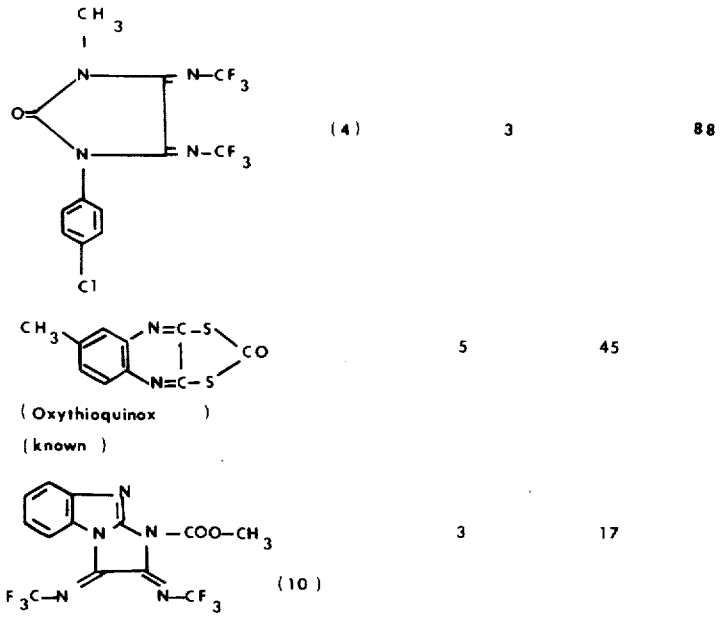

| | | |
|---|---|---|
| (4) | 3 | 88 |
| (Oxythioquinox) (known) | 5 | 45 | 71 |
| (10) | 3 | 17 | 50 |

EXAMPLE 7

Podosphaera test (systemic)

Solvent: 4.7 parts by weight acetone
Dispersing agent: 0.3 parts by weight alkylaryl polyglycol ether
Water: 95 parts by weight The amount of active compound required for the desired concentration of the active compound in the liquid to be used for watering is mixed with the stated amount of solvent, and the concentrate is diluted with the stated amount of water which contains the stated additions.

Apple seedlings grown in standard soil are, in the 3–4 leaf stage, watered in one week with 20cc of the liquid to be used for watering, in the stated concentration of active compound, with reference to 100cc of soil. The plants so treated are, after the treatment, inoculated with conidia of Podosphaera leucotricha Salm and placed in a greenhouse at a temperature of 21°–23°C and at a relative atmospheric humidity of about 70%. 10 days after the inoculation, the infection of the seedlings is determined as a percentage of the untreated but also inoculated control plants.

0% means no infection; 100% means that the infection is exactly as great as in the case of the control plants.

The active compounds, the concentrations of the active compounds and the results obtained can be seen from the following Table 8:

Table 7

Podosphaera-Test/systemic

| Active compound | Infection as a percentage of the infection of the untreated control with a concentration of active compound of | |
|---|---|---|
| | 30 ppm | 15 ppm |

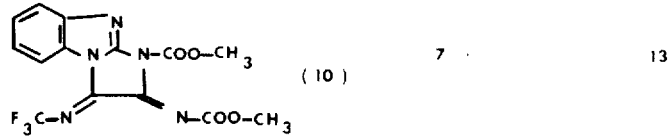

| | | |
|---|---|---|
| (10) | 7 | 13 |

EXAMPLE 8

Agar plate test

Test for fungitoxic effectiveness and breadth of the activity spectrum.

Solvent: Acetone
Parts by weight: a) 1000  b) 100

To produce a suitable preparation of the active compound, 1 part by weight of the active compound is taken up in the stated amount of solvent.

To potato dextrose agar which has been liquefied by heating there is added the preparation of the active compound in such an amount that the desired concentration of active compound is set up therein. After thorough shaking to achieve a uniform dispersion of the active compound, the agar is poured into Petri dishes under sterile conditions. When the mixture of substrate and active compound has solidified, test fungi from pure cultures are inoculated on to it in small discs of 5 mm diameter. The Petri dishes remain at 20°C for 3 days for incubation.

After this time, the inhibiting action of the active compound on the mycelium growth is determined in categories, taking into account the untreated control. 0 means no mycelium growth, either on the treated substrate or on the inoculum; the symbol − means mycelium growth on the inoculum only but no spread to the treated substrate; and the symbol + means mycelium growth from the inoculum on to the treated substrate, similar to the spread to the untreated substrate of the control.

The active compounds, the concentration of the active compounds, the test fungi and the inhibition effects achieved can be seen from the following Table 5.

Table 8

Agar plate test

| Active compound | | Concentration of active compound in the substrate in ppm | A | B | C | D | E | F | G | H |
|---|---|---|---|---|---|---|---|---|---|---|
| untreated | | − | + | + | + | + | + | + | + | + |
| $CH_2-NHCS-Zn-CH_2-NHCS$ (known) | (B) | a) 10 | + | + | + | + | + | + | + | + |
| | | b) 100 | + | + | + | 0 | + | + | + | + |
| [compound] | (1) | a) 10 | 0 | 0 | 0 | 0 | 0 | 0 | 0 | 0 |
| | | b) 100 | 0 | 0 | 0 | 0 | 0 | 0 | 0 | 0 |
| [compound] | (4) | a) 10 | 0 | 0 | − | − | 0 | 0 | 0 | − |
| | | b) 100 | 0 | 0 | 0 | − | 0 | 0 | 0 | − |
| [compound] | (5) | a) 10 | 0 | 0 | 0 | 0 | 0 | 0 | 0 | 0 |
| | | b) 100 | 0 | 0 | 0 | 0 | 0 | 0 | 0 | 0 |
| [compound] | (7) | a) 10 | 0 | 0 | + | − | 0 | 0 | + | + |
| | | b) 100 | 0 | 0 | + | − | 0 | 0 | 0 | + |

A *Corticium rolfsii*
B *Sclerotinia sclerotiorum*
C *Verticillium alboatrum*
D *Thielaviopsis basicola*
E *Phytophthora cactorum*
F *Fusarium culmorum*
G *Fusarium oxysporum*
H *Fusarium solani f. pisi*

EXAMPLE 9

Erysiphe test/systemic

Solvent: 4.7 parts by weight acetone
Emulsifier: 0.3 parts by weight alkylaryl polyglycol ether
Water: 95 parts by weight The amount of the active compound required for the desired concentration in the liquid to be used for watering is mixed with the stated amount of the solvent, and the concentration is diluted with the stated amount of water containing the stated additions.

Cucumber plants grown in standard soil are, in the one- to two-leaf stage, watered three times in one week with 20 cc of the liquid to be used for watering, in the stated concentration of active compound with reference to 100 cc of soil.

The plants so treated are, after the treatment, inoculated with conidia of the fungus *Erysiphe cichoracearum*. The plants are subsequently placed in a greenhouse at 23°–24°C and at a relative atmospheric humidity of 70%.

After 12 days, the infection of the cucumber plants is determined as a percentage of the untreated but also inoculated control plants. 0% means no infection; 100% means that the infection is exactly as great as in the case of the control plants.

The active compounds, the concentrations of the active compounds and the results obtained can be seen from the following Table 3:

EXAMPLE 10

Seed dressing test/bunt of wheat (seed-borne mycosis)

To produce a suitable dry dressing, the active compound is extended with a mixture of equal parts by weight of talc and kieselguhr to give a finely powdered mixture with the desired concentration of the active compound.

Wheat seed is contaminated with 5 g of the chlamydospores of *Tilletia caries* per kg of seed. To apply the dressing, the seed is shaken with the dressing in a closed glass flask. The seed, on moist loam under a cover of a layer of muslin and 2 cm of moderately moist compost soil, is exposed to optimum germination conditions for the spores for 10 days at 10°C in a refrigerator.

The germination of the spores on the wheat grains, each of which is contaminated with about 100,000 spores, is subsequently determined microscopically. The smaller the number of spores which have germinated, the more effective is the active compound.

The active compounds, the concentrations of the active compounds in the dressing, the amounts of dressing used and the percentage spore germination can be seen from the following Table 6.

Table 9
Erysiphe-Test/systemic

| Active compound | Infection as a percentage of the infection of the untreated control with a concentration of active compound of 30 ppm | 15 ppm |
|---|---|---|
| 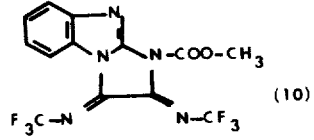 (10) | 0 | 0 |

Table 10
Seed dressing test / bunt of wheat

| Active compounds | Concentration of active compound in the dressing in % by weight | Applied amount of dressing in g/kg seed | Spore germination in % |
|---|---|---|---|
| non-dressed | — | — | >10 |
| CH₂-NHCS\Zn / CH₂-NHCS  (B) (known) | 10 | 1 | 5 |
|  | 30 | 1 | 0.05 |
| (3) | 30 | 1 | 0.05 |

Table 10-continued

Seed dressing test / bunt of wheat

| Active compounds | | Concentration of active compound in the dressing in % by weight | Applied amount of dressing in g/kg seed | Spore germination in % |
|---|---|---|---|---|
| [structure: 1,3-dimethyl analog with 4-Cl-phenyl, N-CF$_3$ groups] | (4) | 10 | 1 | 0.000 |
| | | 30 | 1 | 0.000 |
| [structure: analog with phenyl, N-CF$_3$ groups] | (5) | 30 | 1 | 0.000 |

EXAMPLE 11

Seed dressing test/stripe disease of barley (seed-borne mycosis)

To produce a suitable dry dressing, the active compound is extended with a mixture of equal parts by weight of talc and kieselguhr to give a finely powdered mixture with the desired concentration of active compound.

To apply the dressing, barley seed, which is naturally infested by *Helminthosporium gramineum*, is shaken with the dressing in a closed glass flask. The seed, on moist filter paper discs in closed Petri dishes, is exposed to a temperature of 4°C for 10 days in a refrigerator. The germination of the barley, and possibly also of the fungus spores, is thereby initiated. Two batches of 50 grains of the pregerminated barley are subsequently sown 2 cm deep in Fruhstorfer standard soil and cultivated in a greenhouse at temperatures of about 18°C in seed boxes which are exposed to light for 16 hours daily. The typical symptoms of the stripe disease develop within 3 to 4 weeks.

After this time, the number of diseased plants is determined as a percentage of the total number of emerged plants. The fewer plants are diseased, the more effective is the active compound.

The active compounds, the concentration of the active compounds in the dressing, the amounts of dressing used and the number of diseased plants can be seen from Table 7.

Table 11

Seed dressing test / stripe disease of barley

| Active compound | | Concentration of active compound in the dressing in % by weight | Applied amount of dressing in g/kg seed | Number of stripe-diseased plants as a percentage of the total number of emerged plants |
|---|---|---|---|---|
| non-dressed | | — | — | 23.6 |
| [structure: 1,3-dimethyl, N-CF$_3$ groups] | (1) | 30 | 2 | 3.3 |

EXAMPLE 12

Soil treating agent test/soil-borne mycoses

To produce a suitable preparation of the active compound, the active compound is extended with talc to a content of 5% and subsequently with quartz sand to a content of 0.5% of active compound.

The preparation of the active compound is uniformly mixed with Fruhstorfer standard soil, which has first been sterilized and then inoculated with pure cultures of the test fungi.

The soil is filled into 5 pots, each of which is sown with 10 seeds of the host plants. The pots are placed in a greenhouse at the stated temperature and kept normally moist.

3 weeks after sowing, the number of healthy plants is determined as a percentage of the number of seeds sown. 0% means that no healthy plants have grown; 100% means that healthy plants have resulted from all the seeds.

The active compounds, the concentrations of the active compounds in the soil, the test fungi, host plants, greenhouse temperatures and the results obtained can be seen from Table 8.

stated amount of emulsifier, and the concentrate is diluted with water to the desired concentration.

Table 12

Soil treating agent test / soil-borne mycosis

| Active compounds | Test fungi: | Rhizoct. solani | Fusarium culmorum |
|---|---|---|---|
| | Host plant: | Pea | Pea |
| | Temperature range: | 18–22° | 22–25° |
| | Concentration of active compound in mg/liter soil | | |
| Fruhstorfer standard soil sterilized untreated | | 95 | 90 |
| Frunstorfer standard soil sterilized and inoculated untreated | | 0 | 20 |
| [Zn dithiocarbamate structure] | 100 | 2 | 2 |
| [Structure (1)] | 100 | | 97 |
| | 50 | | 94 |
| | 25 | | 30 |
| [Structure (4)] | 100 | | 76 |

EXAMPLE 13

Phaedon larvae test

Solvent:    3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier, and the concentrate is diluted with water to the desired concentration.

Cabbage leaves (*Brassica oleracea*) are sprayed with the preparation of the active compound until dripping wet and then infested with mustard beetle larvae (*Phaedon cochleariae*).

After the specified periods of time, the degree of destruction is determined as a percentage: 100% means that all the beetle larvae are killed. 0% means that none of the beetle larvae are killed.

The active compounds, the concentration of the active compound, the times of evaluation and the results can be seen from the following Table 9.

To produce a suitable preparation of active compound, 1 part by weight of the active compound is Table 13

(plant-damaging insects)
Phaedon larvae test

| Active compounds | | Concentration of active compound in % | Degree of destruction in % after 3 days |
|---|---|---|---|
| 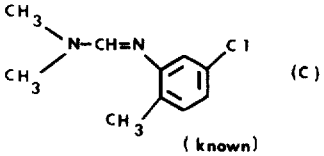 (known) | (C) | 0.2 | 85 |
| | | 0.02 | 0 |
| 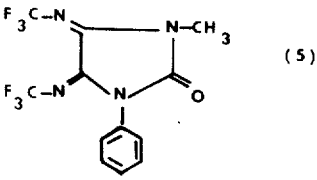 | (5) | 0.2 | 100 |
| | | 0.02 | 70 |
| 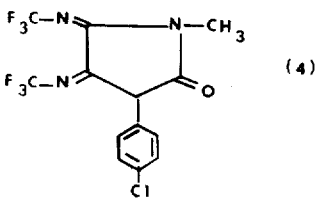 | (4) | 0.2 | 100 |
| | | 0.02 | 30 |
| 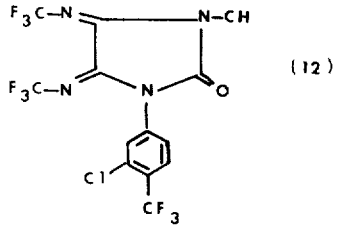 | (12) | 0.2 | 100 |
| | | 0.02 | 30 |
| 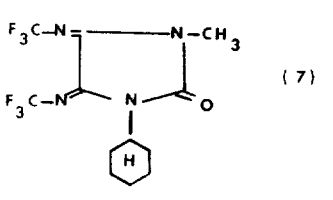 | (7) | 0.2 | 100 |
| | | 0.02 | 70 |

EXAMPLE 14

Tetranychus test (resistant)

Solvent: 3 parts by weight acetone
Emulsifier: 1 part by weight alkylaryl polyglycol ether mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

The active compounds, the concentrations of the active compounds, the evaluation times and the results can be seen from the following Table 10.

Table 14

| Active compounds | (plant-damaging insects) Tetranychus test (resistant) | Concentration of active compound in % | Degree of destruction in % after 8 days |
|---|---|---|---|
| 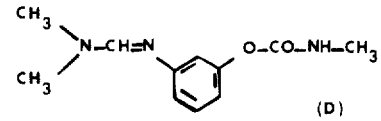 (D) (known) | | 0.2 0.02 | 100 0 |
| 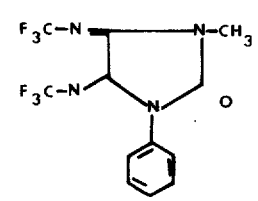 (5) | | 0.2 0.02 | 100 90 |
| 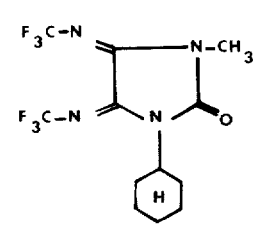 (7) | | 0.2 0.02 | 100 90 |
| 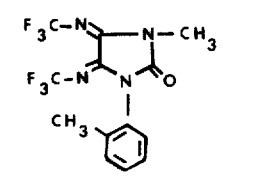 (30) | | 0.1 0.01 | 100 90 |
| 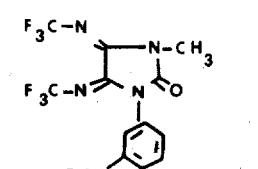 (31) | | 0.1 0.01 | 100 98 |

Table 14-continued
(plant-damaging insects)
Tetranychus test (resistant)
| Active compounds | Concentration of active compound in % | Degree of destruction in % after 8 days |
|---|---|---|
| 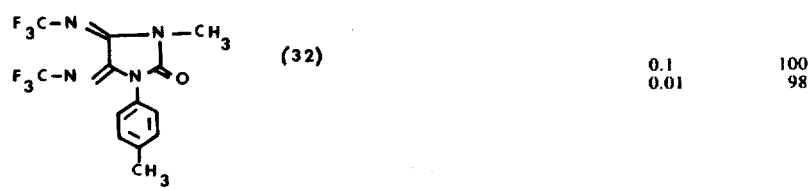 (32) | 0.1<br>0.01 | 100<br>98 |
|  (36) | 0.1<br>0.01 | 100<br>90 |
|  (33) | 0.1<br>0.01 | 100<br>98 |
|  (42) | 0.1<br>0.01 | 100<br>90 |
|  (40) | 0.1<br>0.01 | 100<br>98 |
|  (34) | 0.1<br>0.01 | 100<br>98 |

Table 14-continued (plant-damaging insects)
Tetranychus test (resistant)

| Active compounds | Concentration of active compound in % | Degree of destruction in % after 8 days |
|---|---|---|
| (27) | 0.1<br>0.01 | 100<br>90 |
| (28) | 0.1<br>0.01 | 100<br>98 |
| (8) | 0.1<br>0.01 | 100<br>98 |
| (17) | 0.1<br>0.01 | 100<br>90 |
| (56) | 0.1<br>0.01 | 100<br>98 |
| (63) | 0.1<br>0.01 | 100<br>100 |
| (60) | 0.1<br>0.01<br>0.001 | 100<br>90<br>70 |

Table 14-continued (plant-damaging insects)
Tetranychus test (resistant)

| Active compounds | Concentration of active compound in % | Degree of destruction in % after 8 days |
|---|---|---|
| (52) [structure: F₃C-N, F₃C-N, N-CH₂-CH₂-OCH₃, N=O, phenyl-Cl] | 0.1<br>0.001 | 100<br>100 |
| (22) [structure: F₃C-N, F₃C-N, N-CH₂-CH=CH₂, N-O, phenyl] | 0.1<br>0.01 | 100<br>98 |
| (50) [structure: F₃C-N, F₃C-N, N-cyclohexyl(H), N=O, phenyl-Cl,Cl] | 0.1<br>0.01 | 100<br>98 |
| (67) [structure: F₃C-N, F₃C-N, N-CH₂-CH₂-OCH₃, N=O, phenyl-OCH₃] | 0.1<br>0.01 | 100<br>98 |
| (64) [structure: F₃C-N, F₃C-N, N-CH₂-CH₂-OCH₃, N=O, phenyl-Cl,CH₃] | 0.1<br>0.01 | 100<br>98 |

EXAMPLE 15

Plutella test

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation time and the results can be seen from the following Table 11.

Table 15
(plant-damaging insects)
Plutella test
| Active compounds | | Concentration of active compound in % | Degree of destruction in % after 3 days |
|---|---|---|---|
| 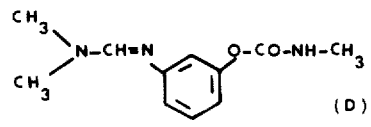 (D) (known) | | 0.2<br>0.02 | 95<br>0 |
| 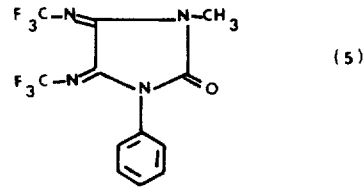 (5) | | 0.2<br>0.02<br>0.002 | 100<br>100<br>50 |
| 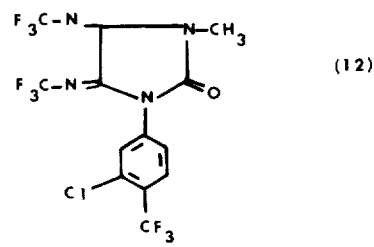 (12) | | 0.2<br>0.02 | 100<br>90 |
| 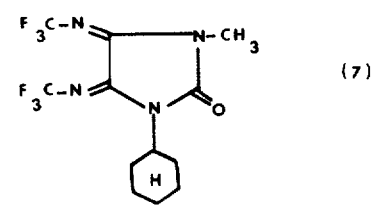 (7) | | 0.2<br>0.02 | 100<br>100 |

The following further examples are set forth to illustrate, without limitation, the process for producing the active compounds according to the present invention.

EXAMPLE 16

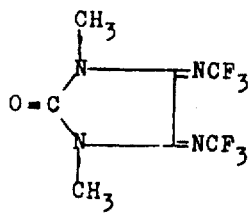
(1)

To 9 g (0.1 mole) of N,N'-dimethyl urea and 15 g (0.36 mole) of sodium fluoride in 150 ml of benzene there are added dropwise, at a temperature of 50°C, 23 g (0.1 mole) of perfluoro-2,5-diazahexa-2,4-diene. Stirring under reflux is afterwards effected for about 30 minutes, followed by filtration from sodium hydrogen fluoride and sodium fluoride and concentration of the filtrate in a vacuum. After recrystallization from ether/pentane there are obtained 19 g 1,3-dimethyl-4,5-bis-trifluoromethylimino-imidazolone-(2) of the melting point 109°-110°C. The yield is 69% of theory.

EXAMPLE 17

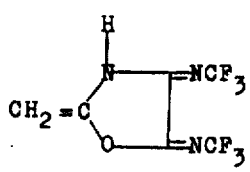
(2)

Analogously with Example 16, with acetamide instead of N,N'-dimethyl urea there is obtained the above compound. The melting point (from ether/pentane) is 90°-92°C (with decomp.) Mass spectrum: 247 m/e.

EXAMPLE 18

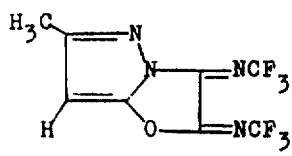
(3)

To 10 g (0.1 mole) of 3-methyl-pyrazolone-(5) and 15 g of sodium fluoride in 100 ml of acetonitrile there are added dropwise, at a temperature of −30°C, 23 g (0.1 mole) of perfluoro-2,5-diazahexa-2,4-diene. Stirring is afterwards effected for 2 hours at 0°C, followed by filtration from sodium hydrogen fluoride and sodium fluoride and concentration of the filtrate in a vacuum. After recrystallization from ether/hexane there is obtained the compound of the above formula of the m.p. 95°-96°C.

Mass spectrum: 286 m/e

EXAMPLE 19

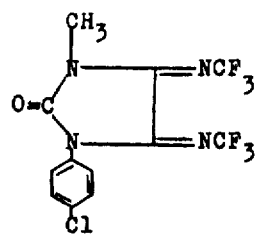
(4)

Analogously with Example 16, with N-p-chlorophenyl-N'-methyl urea instead of N,N'-dimethyl urea there is obtained the compound of the above formula of the m.p. 172°-173°C.

Yield: 92% of theory.

EXAMPLE 20

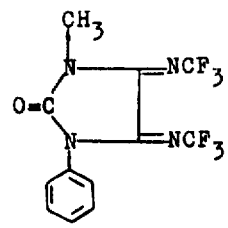
(5)

Analogously with Example 16, with N-phenyl-N'-methyl urea instead of N,N'-dimethyl urea there is obtained the compound of the above formula of the m.p. 159°-160°C.

Yield: 89% of theory.

EXAMPLE 21

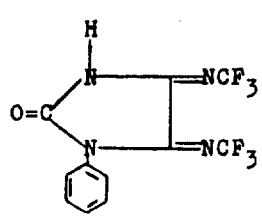
(6)

Analogously with Example 18, with N-phenyl urea instead of 3-methyl-pyrazolone-(5) there is obtained the compound of the above formula of the m.p. 162°–163°C.

EXAMPLE 22

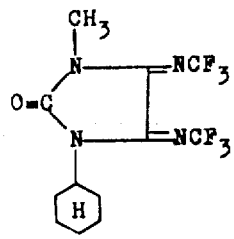 (7)

Analogously with Example 16, with N-cyclohexyl-N'-methyl-urea there is obtained the compound of the above formula of m.p. 135°–136°C. Yield: 70% of theory.

EXAMPLE 23

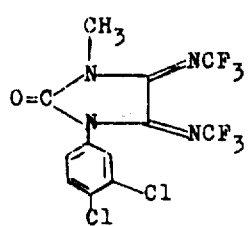 (8)

Analogously with Example 16, with N-3,4-dichlorophenyl-N'-methyl urea there is obtained the above compound of the m.p. 149°–150°C. Yield: 84% of theory.

EXAMPLE 24

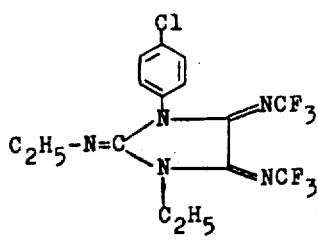 (9)

Analogously with Example 18, with p-chlorophenylimide-N,N'-diethyl urea there is obtained the above compound of the m.p. 95°–96°C. Yield: 69% of theory.

EXAMPLE 25

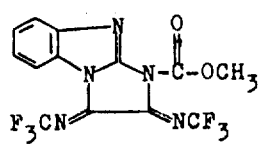 (10)

Analogously with Example 18, with 2-[amino-(carbomethoxy)]-benzimidazole there is obtained the above compound of the m.p. 152°–153°C (decomp.) (from acetone). Yield: 74 % of theory.

EXAMPLE 26

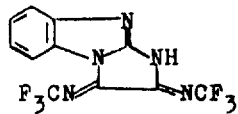 (11)

Analogously with Example 18, with 2-amino-benzimidazole there is obtained the above compound of the m.p. 175°C (with decomposition). Yield: 70% of theory.

EXAMPLE 27

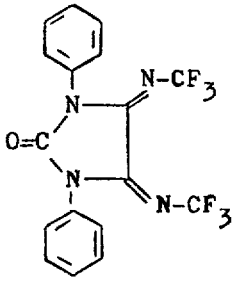 (12)

Analogously with Example 16, with N-(3-chloro-4-trifluoromethyl)-phenyl-N'-methyl urea there is obtained the above compound of the m.p. 95°–96°C. Yield: 75% of theory.

EXAMPLE 28

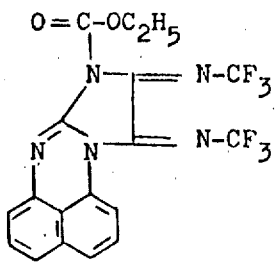 (13)

Analogously with Example 16, with N,N'-diphenyl urea there is obtained the compound of the above formula of m.p. 197° to 198°C. Yield: 70% of theory.

EXAMPLE 29

(14)

Analogously with Example 18, with 2-perimidinecarbamic acid ethyl ester there is obtained the compound of the above formula of m.p. 150°C (decomp). Yield: 73% of theory.

EXAMPLE 30

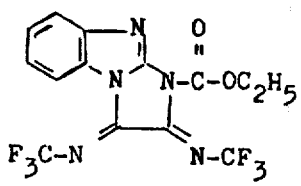                                    (15)

Analogously with Example 18, with 2-amino-(carboethoxy)-benzimidazole there is obtained the above compound of m.p. 108°C (decomp). Yield: 76% of theory.

In analogous manner there were prepared the following compounds:

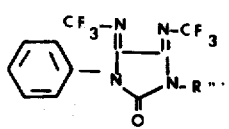

| Compound No. | R'''' | m.p. (°C) |
|---|---|---|
| 16 | C₂H₅ | 161 |
| 17 | C₃H₇ | 138 |
| 18 | i—C₃H₇ | 130 |
| 19 | C₄H₉ | 145 |
| 20 | i—C₄H₉ | 135 |
| 21 | t—C₄H₉ | 143–147 |
| 22 | CH₂—CH=CH₂ | 136 |
| 23 | —⟨H⟩ | 181 |
| 24 | —CH₂—CH₂—OCH₃ | 143 |
| 25 | —(CH₂)₃—CN | 94 |
| 26 | —CH₂-CH₂-⟨ ⟩ | 133 |

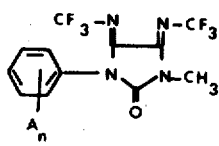

| Compound No. | Aₙ | m.p. (°C) |
|---|---|---|
| 27 | 2—Cl | 102–104 |
| 28 | 3—Cl | 131 |
| 29 | 3—Cl, 5—Cl | 167 |
| 30 | 2—CH₃ | 116 |
| 31 | 3—CH₃ | 127 |
| 32 | 4—CH₃ | 116 |
| 33 | 4—C₂H₅ | 114 |
| 34 | 3—OC₂H₅ | 115 |
| 35 | 4—OC₂H₅ | 148 |
| 36 | 3—CH₃, 4—CH₃ | 108–110 |
| 37 | 2—Cl, 4—Cl | 122 |
| 38 | 2—CH₃, 6—CH₃ | 138 |
| 39 | 2—C₂H₅, 6—C₂H₅ | 107 |
| 40 | 2—OCH₃ | 107 |
| 41 | 2—CH₃, 3—CH₃ | 120 |
| 42 | 2—i—C₃H₇ | 82–86 |
| 43 | 2—CH₃, 4—CH₃, 5—CH₃ | 150 |
| 44 | 3—OCH₃ | 116–118 |
| 45 | 2—CH₃, 4—Cl | 148 |

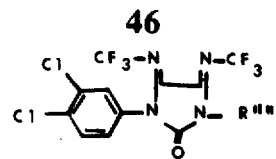

| Compound No. | R'''' | m.p. (°C) |
|---|---|---|
| 46 | C₂H₅ | 124–126 |
| 47 | C₃H₇ | 114–117 |
| 48 | i—C₃H₇ | 114–117 |
| 49 | C₄H₉ | 120–122 |
| 50 | —⟨H⟩ | 102–105 |
| 51 | CH₂—⟨ ⟩ | 89–95 |
| 52 | —CH₂—CH₂—OCH₃ | 76–78 |

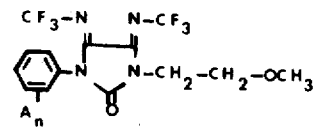

| Compound No. | Aₙ | m.p. (°C) |
|---|---|---|
| 53 | 2—Cl, 4—Cl | 115 |
| 54 | 2—CH₃ | 113 |
| 55 | 4—OC₂H₅ | 121 |
| 56 | 4—CH₃ | 118 |
| 57 | 3—CH₃ | 107 |
| 58 | 4—Cl | 122 |
| 59 | penta Cl | 108–111 |
| 60 | 2—i—C₃H₇ | 74–76 |
| 61 | 2—CH₃, 4—CH₃ | 115–118 |
| 62 | 2—CH₃, 3—CH₃ | 88–92 |
| 63 | 2—C₂H₅ | 74–76 |
| 64 | 3—Cl, 4—CH₃ | 97–98 |
| 65 | 2—C₂H₅, 6—C₂H₅, 3—Cl, 4—Cl, 5—Cl | 84–85 |
| 66 | 2—OCH₃, 4—Cl, 5—CH₃ | 101–102 |
| 67 | 2—OCH₃ | 71–73 |
| 68 | 3—OCH₃ | 108–111 |
| 69 | 3—OCH₃, 4—CH₃ | 115–117 |
| 70 | 3—CN | 120–121 |
| 71 | 3—NO₂ | 125–127 |

| Compound No | Formula | m.p. (°C) |
|---|---|---|
| 72 | 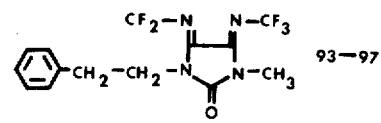 | 93–97 |
| 73 | 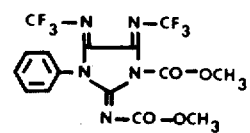 | 174–175 |

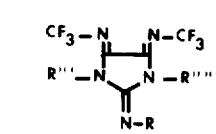

| Compound No. | R | R''' | R'''' | m.p. (°C) |
|---|---|---|---|---|
| 74 | CO—OCH₃ | C₆H₅—CH₂ | CO—OCH₃ | 122–123 |
| 75 | CO—OCH₃ | CH₃—O—C₆H₄— | CO—OCH₃ | 190 (decomp.) |
| 76 | CO—OCH₃ | 2,6-Cl₂—C₆H₃— | CO—OCH₃ | 157 (decomp.) |
| 77 | —C₆H₅ | —C₆H₅ | CH₃ | 157 |

It will be appreciated that the instant specification and examples are set forth by way of illustration and not limitation, and that various modifications and changes may be made without departing from the spirit and scope of the present invention.

What is claimed is:

1. A fungicidal, insecticidal or acaricidal composition comprising a fungicidally, insecticidally or acaricidally effective amount of a compound of the formula

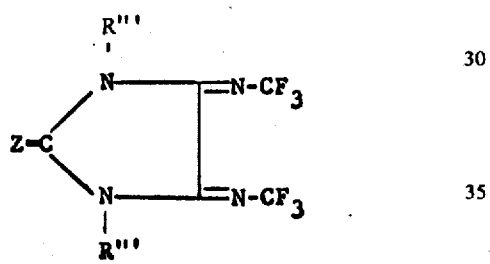

in which

Z is oxygen, R—N= or

and

R, R', R" and R''' are each hydrogen; alkyl, alkenyl or alkynyl with up to 8 carbon atoms optionally substituted by halogen, cyano, lower alkoxy or alkylmercapto; optionally lower-alkyl-substituted cycloalkyl; carbalkoxy containing up to 5 carbon atoms in the alkoxy group; aralkyl with up to 2 carbon atoms in the alkyl moiety or aryl with up to 14 carbon atoms in the ring system, the aryl radicals optionally being substituted by halogen, cyano, nitro, lower alkyl, lower haloalkyl, lower alkoxy or lower alkylmercapto; or a radical which together with Z or an N-atom of the ring forms a further 5- or 6-membered ring containing two nitrogen atoms and optionally fused with a benzene ring which is optionally partially hydrogenated.

2. A composition according to claim 1 wherein such compound is

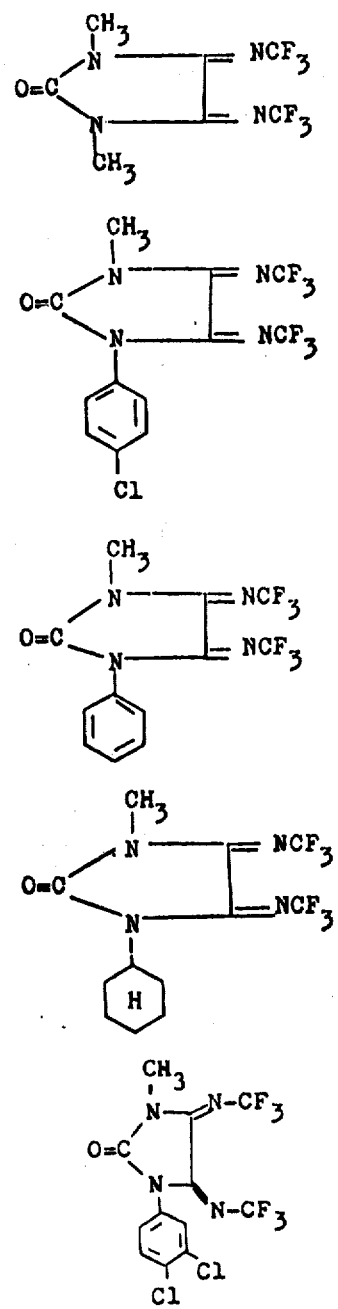

49

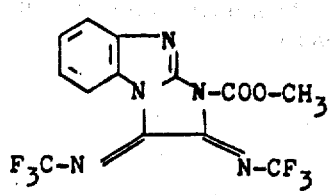

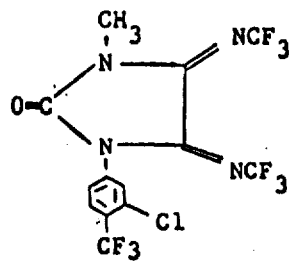

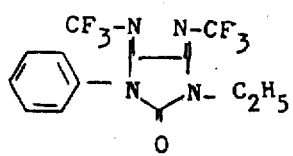

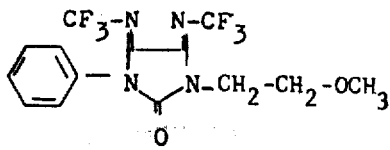

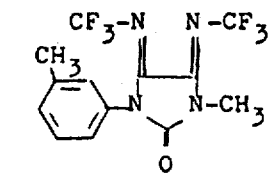

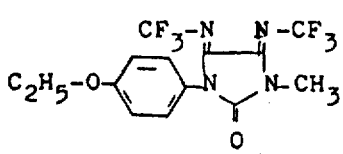

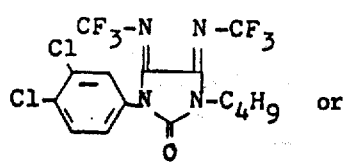 or

50

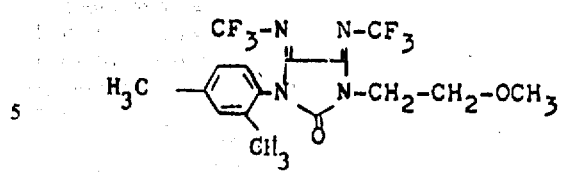

3. A method of combating fungus, insect or acarid pests which comprises applying to the pests or a habitat thereof a fungicidally, insecticidally or acaricidally effective amount of a compound of the formula

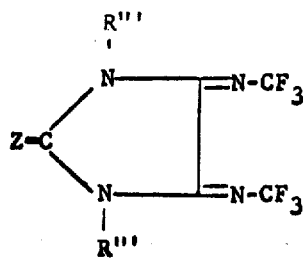

in which
Z is oxygen, R—N= or

and
R, R', R'' and R''' are each hydrogen; alkyl, alkenyl or alkynyl with up to 8 carbon atoms optionally substituted by halogen, cyano, lower alkoxy or alkylmercapto; optionally lower-alkyl-substituted cycloalkyl; carbalkoxy containing up to 5 carbon atoms in the alkoxy group; aralkyl with up to 2 carbon atoms in the alkyl moiety or aryl with up to 14 carbon atoms in the ring system, the aryl radicals optionally being substituted by halogen, cyano, nitro, lower alkyl, lower haloalkyl, lower alkoxy or lower alkylmercapto; or a radical which together with Z or an N-atom of the ring forms a further 5- or 6-membered ring containing two nitrogen atoms and optionally fused with a benzene ring which is optionally partially hydrogenated.

4. The method of claim 3 in which R, R', R'' and R''' are hydrogen, alkyl or alkenyl with up to 6 carbon atoms, optionally substituted by fluorine, chlorine, bromine or alkylmercapto; cyclopentyl or cyclohexyl; carbalkoxy containing up to 5 carbon atoms in the alkoxy group; benzyl or aryl with up to 10 carbon atoms in the ring system, the aromatic rings being optionally substituted by fluorine, chlorine, bromine, cyano, nitro, methyl, ethyl, isopropyl, chloromethyl, trifluoromethyl, methoxy or methylmercapto; or a radical which together with Z or an N-atom of the ring forms a further 5- or 6-membered ring optionally fused with a benzene ring which may be partially hydrogenated.

5. The method of claim 3 in which Z is oxygen, and each R''' independently is alkyl of up to 8 carbon atoms, cyclopentyl, cyclohexyl, phenyl, or phenyl mono- or di-substituted with halo, nitro, CF₃, lower alkyl, lower alkoxy or loweralkylthio.

6. The method of claim 3 wherein the compound has the formula

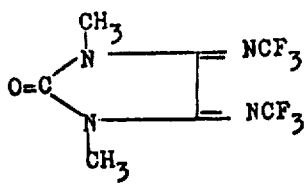

7. The method of claim 3 wherein the compound has the formula

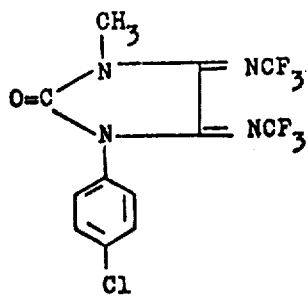

8. The method of claim 3 wherein the compound has the formula

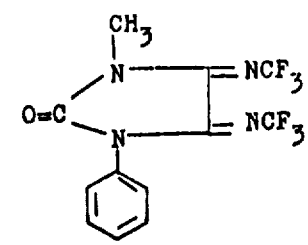

9. The method of claim 3 wherein the compound has the formula

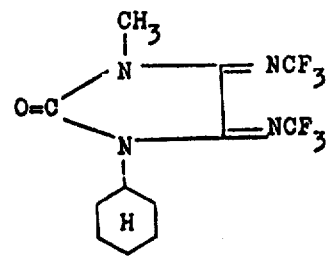

10. The method of claim 3 wherein the compound has the formula

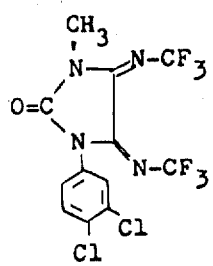

11. The method of claim 3 wherein the compound has the formula

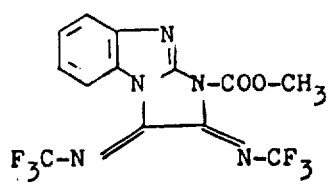

12. The method of claim 3 wherein the compound has the formula

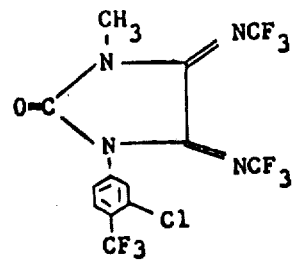

13. The method of claim 3 wherein the compound has the formula

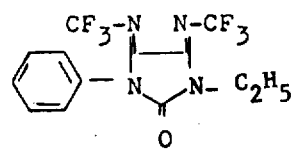

14. The method of claim 3 wherein the compound has the formula

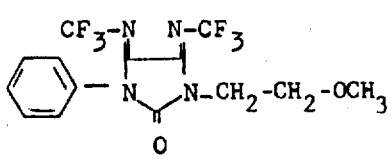

15. The method of claim 3 wherein the compound has the formula
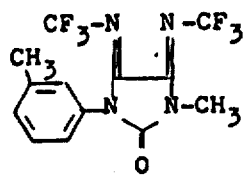
16. The method of claim 3 wherein the compound has the formula
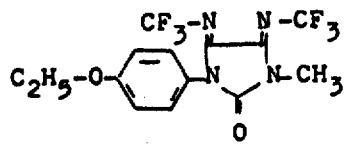
17. The method of claim 3 wherein the compound has the formula
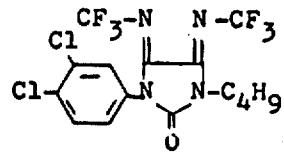
18. The method of claim 3 wherein the compound has the formula
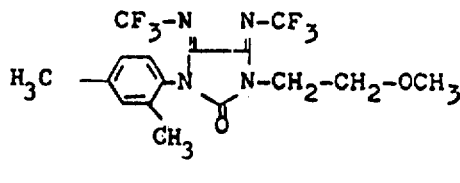
* * * * *